US00PP22468P2

(12) United States Plant Patent
Quinn

(10) Patent No.: US PP22,468 P2
(45) Date of Patent: Jan. 24, 2012

(54) ***MISCANTHUS* PLANT NAMED 'HURON STAR'**

(50) Latin Name: *Miscanthus sinensis*
Varietal Denomination: Huron Star

(76) Inventor: Martin Quinn, Goderich (CA)

( * ) Notice: Subject to any disclaimer, the term of this patent is extended or adjusted under 35 U.S.C. 154(b) by 0 days.

(21) Appl. No.: 12/806,687

(22) Filed: Aug. 19, 2010

(51) Int. Cl.
*A01H 5/00* (2006.01)

(52) U.S. Cl. ..... Plt./384

(58) Field of Classification Search ..... Plt./384
See application file for complete search history.

*Primary Examiner* — Annette Para

(57) ABSTRACT

The new and distinct hybrid of ornamental Maiden Grass plant cultivar of *Miscanthus sinensis* plant named Huron Star' has a tall upright habit and light colored flowers well above the foliage that develops a purplish tinting later in the season.

1 Drawing Sheet

Botanical classification: *Miscanthus sinensis*.
Variety denomination: 'Huron Star'.

BACKGROUND AND ORIGIN OF THE PLANT

*Miscanthus sinensis* 'Huron Star', hereinafter also referred to as 'Huron Star' and the "plant" is a new and distinct cultivar of Maiden Grass. It was an intentional cross by Martin D. Quinn in 2002 between *Miscanthus sinensis* 'Silberfeder' (not patented)×*Miscanthus sinensis* 'Huron Blush' (not patented) at a nursery in Kincardine, Ontario, Canada, selected for further observation in 2004 and selected for final introduction in 2006. The purpose of the cross was to obtain taller, earlier flowering *Miscanthus* cultivars. The plant has been successfully asexually propagated by many successive divisions since 2006 at the same perennial plant nursery in Kincardine, Ontario, Canada and found to produce identical plants that maintain the unique characteristics of the original plant. The plant is stable and reproduces true to type in successive generations of asexual reproduction.

SUMMARY AND GENERAL DESCRIPTION OF THE PLANT

*Miscanthus* 'Huron Star' differs from its parents as well as all other *Miscanthus* known to the applicant. The new plant flowers about three weeks prior to 'Huron Blush' and six weeks prior to 'Silberfeder'. 'Huron Star' is also taller and has a pink flower compared to the white flower of 'Silberfeder' by being taller. The most similar known *Miscanthus* cultivar in flower is *Miscanthus* 'Graziella' (not patented) which has more narrow foliage and is much shorter in height. Other similar cultivars include: 'Huron Sentinel' (not patented) which has a more tawny colored flowers and less white than 'Huron Star'. The new plant is different from these cultivars and all others known to the applicant in the following traits:

1. The flowers and seeds are very light, especially later in the season.
2. The flowers are well above the foliage.
3. The habit is upright and tall.
4. Foliage develops a purplish tinting later in the season.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, intensity, source and direction may cause the appearance of minor variation in color.

DETAILED BOTANICAL DESCRIPTION

Figure 1:
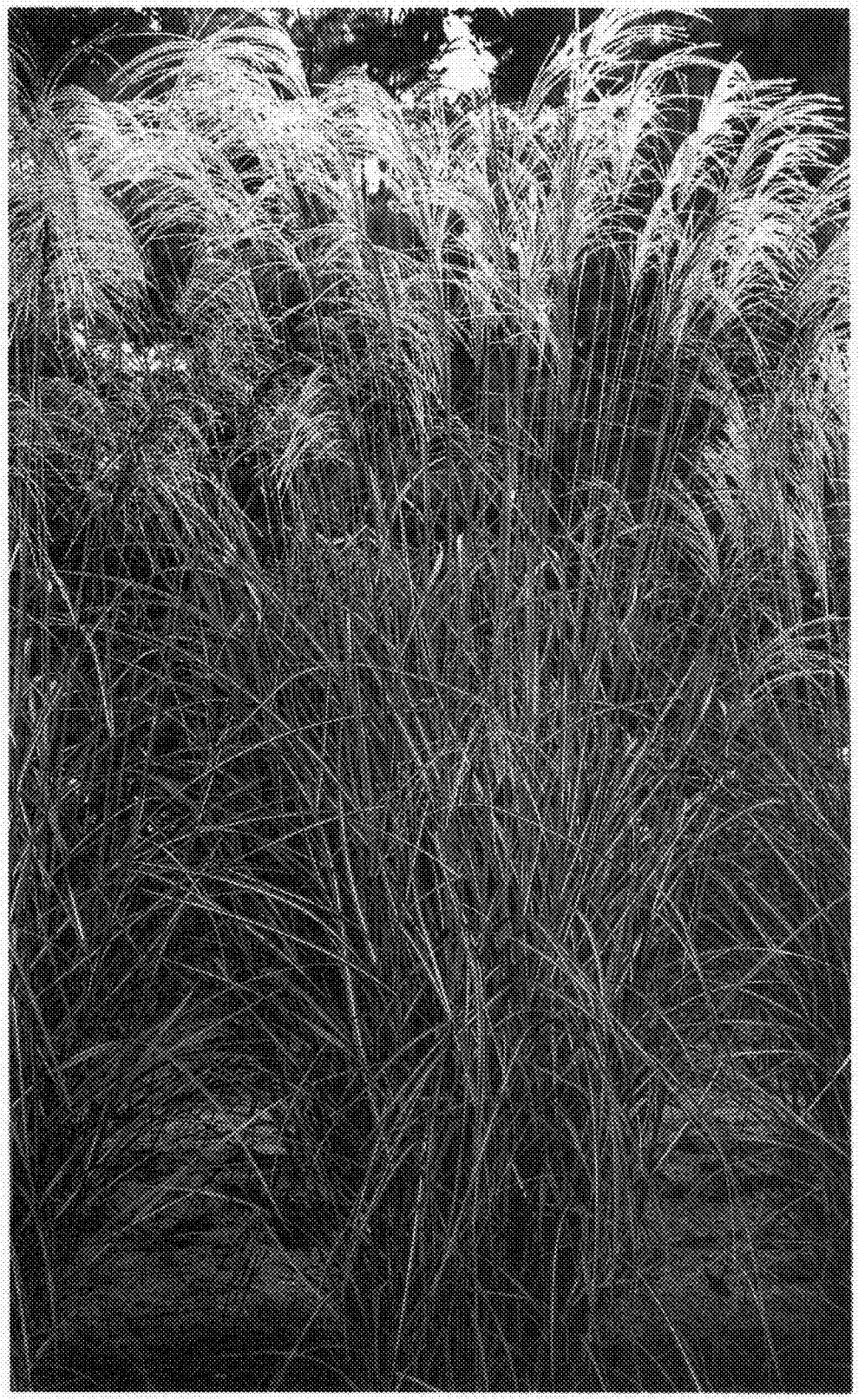
FIG. 1 shows a five-year old plant in flower in early fall having developed the purplish tinting.

The following descriptions and color references are based on the 2001 edition of The Royal Horticultural Society Colour Chart except where common dictionary terms are used. The new plant, 'Huron Star', has not been observed under all possible environments. The phenotype may vary slightly with different environmental conditions, such as temperature, light, fertility, moisture and maturity levels, but without any change in the genotype. The following observations and size descriptions are of a three-year old plant in a trail garden in Zeeland, Mich. in full sun with supplemental water and fertilizer.

Parentage: *Miscanthus sinensis* 'Silberfeder' (not patented) female or seed parent×*Miscanthus sinensis* 'Huron Blush' (not patented) as the male or pollen parent;

Propagation method: By division of the culms in the springtime;

Time to finishing in a three-liter pot: Three months;

Rooting habit: Normal, coarse, branching;

Plant description: Hardy herbaceous perennial forming tightly rhizomatous clump, with upright culms and mostly arching leaves;

Plant size: Foliage height before flowering is 155 to 165 cm tall from soil line to the top of the leaves and 30 to 45 cm wide at soil line and 110 to 125 cm at widest point just below flowers; height with panicles about 205 cm;

Foliage description: Linear, alternate, glaucous, minutely sericeous on abaxial side, random microscopically sericeous on adaxial side; microscopically serrulate margin, conduplicate along center vein, mostly erect to arching toward tips and outer most leaves; sheathed from node of attachment to ligule, deciduous but persist through winter;

Foliage size: 60 to 75 cm long, averaging 64 cm; 10 to 13 mm wide with average about 8 mm wide;

Leaf Color: Main portion nearest RHS 137A on top and nearest RHS 137B underneath; without horizontal banding; later in the growing season the foliage takes on a purplish tinting of nearest RHS N187C;

Ligule: Fringed membranous, glaucous, glabrous except for 2 to 3 mm in width with very fine marginal white hairs about 3 to 6 mm long; encircles about one half the culm; but glabrous on outer surface; color variable with upper ligule portion nearest RHS 164D and along lower edge nearest RHS 165A, with more pigmenting on culms and in regions with more sunlight exposure;

Veins: Parallel, color same as the surrounding leaf on both the top and bottom of the leaf; Center vein: about 2 mm wide and more white than RHS 155D on top and RHS 137B on back;

Culm: Erect, cylindrical, about half enclosed by leaf sheath, 70 to 80 cm long without panicle and about 8.0 mm wide at base; internode length 5 to 7 cm;

Flower description: Basally fan-branched panicle, one panicle per culm, beginning late Summer; drying on plants but persisting through winter; no fragrance detected;

Panicle: Basally fan-branched, 90 to 100 cm long, 30 to 32 cm wide at widest portion; beginning nearest RHS 182D and developing to nearest RHS 159B;

Spikelet: Paired, with several short awns;

*Gynoecium.*—Stigma: two, feathered, protruding about 2 mm from glume;

*Androecium.*—Filaments: fine, hair-like, white, less than 1 mm diameter and up to 2.0 mm long; Anther: 2.0 to 3.0 mm long and about 1.0 mm wide; Pollen: ovoid, less than 0.2 mm in longest dimension;

Fruit: Caryopsis; 2 to 3 mm long and 1.5 mm wide, nearest RHS 164D.

Hardiness, pest and disease resistance: The plant grows best with plenty of moisture and adequate drainage, but is able to tolerate some drought when mature. Hardiness at least from USDA zone 5 through 9. Disease and pest resistance beyond what is typical of that of other Maiden Grasses has not been observed.

I claim:

1. A new and distinct ornamental Maiden Grass plant cultivar of *Miscanthus sinensis* plant named Huron Star' as herein described and illustrated, with tall upright habit and light colored flowers well above the foliage that develops a purplish tinting later in the season, suitable as a potted plant, for the garden, and for cut flower arrangements.

* * * * *